United States Patent [19]
Weinmann et al.

[11] Patent Number: 4,719,098
[45] Date of Patent: Jan. 12, 1988

[54] ENTERAL CONTRAST MEDIUM USEFUL FOR NUCLEAR MAGNETIC RESONANCE IMAGING AND ITS PREPARATION

[75] Inventors: Hanns-Joachim Weinmann; Heinz Gries; Heinrich Michel, all of Berlin, Fed. Rep. of Germany

[73] Assignee: Schering Aktiengesellschaft, Berlin and Berkgamen, Fed. Rep. of Germany

[21] Appl. No.: 946,615

[22] Filed: Dec. 29, 1986

Related U.S. Application Data

[63] Continuation of Ser. No. 607,108, May 4, 1984.

[30] Foreign Application Priority Data

May 4, 1983 [DE] Fed. Rep. of Germany ....... 3316703

[51] Int. Cl.$^4$ .................. A61K 49/00; A61B 5/05; A61B 6/00
[52] U.S. Cl. ........................................ 424/9; 436/806; 128/653; 128/654
[58] Field of Search ............... 424/4, 9; 128/653, 654; 436/173, 806

[56] References Cited

U.S. PATENT DOCUMENTS 3,832,457 8/1974 Sugimoto et al. .................. 424/4
4,615,879 10/1986 Runge et al. ....................... 424/9

FOREIGN PATENT DOCUMENTS 0071564 2/1983 European Pat. Off. .
2361143 6/1974 Fed. Rep. of Germany .......... 424/4

OTHER PUBLICATIONS

France Patent, Brevet Special de Medicament, No. 4,679M, Radioscopic Contrast Agent, 01/23/1967.
Runge et al., Radiology, vol. 147, (1983), pp. 789–791.
The Merck Index, 9th Edition, (1976), p. 789, No. 5915.
Rayudu, G., Radiotracers for Medical Applications, vol. 1, (1983), p. 148, 176.
Biological Abstracts, Band 78, Nr., 3, 1984, Seite 2515, Zusammenfassung Nr. 22904; R. Grossman et al.: "Gadolinium enhanced NMR Images of Experimental Brain Abscess", & J. Comput. Assist. Tomogr. 8(2):204–207, 1984.
Chemical Abstracts, Band 99, Nr. 7, 15. Aug. 1983, Seite 232, Zusammenfassung Nr. 49843k, Columbus Ohio, US; V. M. Runge et al.: "Work in Progress: Potential Oral and Intravenous Paramagnetic NMR Contrast Agents", & Radiology (Easton, Pa.) 1983, 147(3), 798–791.

*Primary Examiner*—Robert J. Warden
*Assistant Examiner*—Stephen C. Wieder
*Attorney, Agent, or Firm*—Millen & White

[57] ABSTRACT

An enteral contrast medium useful for proton nuclear spin tomography contains at least one physiologically compatible paramagnetic compound in combination with a physiologically compatible, osmotically active substance, as well as a physiologically compatible base/buffer or buffer mixture with a pH value of 3 to 8, and, optionally, also a viscosity-raising material, all dissolved or suspended in water. It is excellently suitable for enhancing contrast in imaging, e.g., of the gastrointestinal tract by nuclear spin tomography.

24 Claims, No Drawings

ENTERAL CONTRAST MEDIUM USEFUL FOR NUCLEAR MAGNETIC RESONANCE IMAGING AND ITS PREPARATION

This application is a continuation of application Ser. No. 607,108, filed May 4, 1984.

BACKGROUND OF THE INVENTION

This invention relates to novel enteral contrast media useful for proton nuclear spin tomography (proton NMR diagnosis).

Nuclear spin tomography has developed into a novel and very efficient imaging method for diagnostic purposes, superior to the known diagnostic methods (e.g., X-ray diagnostics, X-ray computerized tomography etc.) in solving certain diagnostic problems.

One advantage of nuclear spin tomography is its excellent suitability for differentiation of tissues. The information content of the image is significantly enhanced by the use of contrast media in nuclear spin tomography. In this connection, novel, iodine-free contrast media, in part used in very low doses, can be utilized. These are substantially more compatible than iodine-containing contrast media. The contrast media lending themselves to nuclear spin tomography exhibit the property, due to their paramagnetism, of affecting the relaxation times $T_1$ (spin-lattice) and $T_2$ (spin-spin) of the hydrogen atoms present in body water in such a way that imaging when using a nuclear spin tomograph is substantially improved.

However, since the possibility of obtaining an image of tissues by nuclear spin tomography exists only if there are sufficient hydrogen atoms (water, fat), body cavities can be reproduced by nuclear spin tomography only if they are filled with an adequate amount of water or fat and if this liquid quantity can be maintained within the area to be diagnosed during the imaging period. Similarly, only in this case is it possible for the paramagnetic contrast medium to deploy its effect. The heretofore described contrast media for nuclear spin tomography are suitable only for imaging tissues having adequate water or fat content.

SUMMARY OF THE INVENTION

Accordingly, it is an object of the present invention to provide new contrast media suitable for use in nuclear spin tomography by enteral administration.

Upon further study of the specification and appended claims, further objects and advantages of this invention will become apparent to those skilled in the art.

These objects have been achieved by the present invention by providing an orally and/or rectally administrable aqueous paramagnetic contrast medium, e.g., solution, containing an osmotically active material, and a base/buffer or buffer substance having a pH value of 3-8, preferably 5-8, whereby a longer lasting image, e.g., of the gastrointestinal tract is obtainable enhanced by the paramagnetic contrast medium.

DETAILED DISCUSSION

By the simultaneous administration of the osmotically active material in accordance with this invention, a solution is produced in the gastrointestinal tract that is iso- and/or hypertonic with respect to the surrounding body fluids. This ensures a sufficiently high osmotic pressure of the contrast medium solution with respect to the surrounding fluids, e.g., those in and behind the membranous tissues forming or adjacent to the gastrointestinal tract walls, to prevent or strongly retard the absorption out of the gastrointestinal tract of water required for imaging.

The osmotically active material of this invention, consequently, is one which causes the osmotic pressure inside the local region of the contrast medium of this invention when in the body after enteral administration to be essentially the same as or higher than that of surrounding fluids during its passage through the gastrointestinal tract. This effect causes a tendency of the surrounding water (e.g., in body tissues) to flow into the region of the contrast medium or at least causes a tendency of the water at the location of the contrast medium not to flow away, e.g., be absorbed by the surrounding tissue. The osmotically active material, for example, can be described as an agent to which the membranous tissue surrounding the gastrointestinal tract is essentially impermeable, thus providing the described osmotic effect. That is, it may be described as an agent which is substantially not absorbed out of the gastrointestinal tract, e.g., which is absorbed by the gastrointestinal tract tissue to an extent of only about 0-50 wt %.

Suitable such pharmacologically acceptable osmotically active materials include polyols and sugars, for example, mannitol, sorbitol, arabitol, and xylitol; mannitol and sorbitol being preferred.

The concentration of the osmotically active material is an amount effective to achieve the osmotic effect described above, usually 5-70 g per liter, preferably 30-50 g per liter of the contrast medium.

In the absence of the osmotically active additive, the water administered with the contrast medium solution is quickly absorbed whereby the amount of hydrogen atoms required for signaling is rapidly decreased. This leads to an increase in concentration of the paramagnetic compound; this increase, in turn, results in a reduction or complete loss of signal intensity during the passage of the contrast medium through the intestinal tract. Accordingly, the paramagnetic contrast media of the prior art used for nuclear spin tomography, when utilized orally, are suitable only for providing contrast in the stomach. Upon oral administration, only a brief imaging of the gastrointestinal tract is possible since the water taken in with the contrast medium solution is quickly absorbed by the gastrointestinal tract. This deficiency of the prior art has created a strong need for making available a paramagnetic contrast mecium suitable for nuclear spin tomography which provides a longer-lasting contrasting of the gastrointestinal tract.

According to this invention, all physiologically compatible paramagnetic compounds are suitable for use in the contrast medium of this invention, especially iron-(III) compounds, such as iron(III) ammonium citrate,
iron(III) glycerophosphate, or
iron(III) sulfate, as well as the paramagnetic complex salts disclosed, for example, in German Laid-Open application No. P 31 29 906 and in German patent application No. 3,401,052 of Jan. 11, 1984 claiming the inner priority of No. P 33 02 410, corresponding to U.S. Ser. No. 401,594 of July 26, 1982 and its CIP Application Ser. No. 573,184 of Jan. 23, 1984 both of whose entire disclosures are incorrorated by reference herein. These include the di-N-methylglucamine salt of the gadolinium(III) complex of diethylenetriamine pentaacetic acid (DTPA), the disodium salt of the gadolinium(III) complex of DTPA, the N-methylglucaminesodium mixed salt of DTPA, the di-N-methylglucamine salt of the iron(III) complex of DTPA, and the sodium salt of the iron(III) complex of ethylenediaminetetraacetic acid (EDTA), wherein the di-N-methylglucamine salt of the gadolinium (III) complex of DTPA is preferred. See also "Handbuch Der Anorganischen Chemie", Rare Earth Elements, Part D1, Page 203, Springer Verlag Berlin, 1980.

Insofar as any physiologically compatible paramagnetic complex salt is described in the literature, it can be produced according to methods known to those skilled in the art, e.g., as demonstrated by the preparation example below. Since the mono-N-methylglucamine salts can be more readily isolated and handled, these are preferably initially prepared, and then an additional equivalent(s) of N-methylglucamine is added during the use of these mono salts to neutralize any free acid equivalents remaining on the particular ligand involved.

Preparation of the Mono-N-methylglucamine Salt of the Iron(III) Complex of Diethylenetriamine Pentaacetic Acid.

23.6 g (60 millimoles) of diethylenetriamine pentaacetic acid is suspended in a solution of 16.6 g (60 mmol) of iron(III) chloride hexahydrate ($FeCl_3 \cdot 6H_2O$, 98% strength) in 500 ml of water. Under intensive agitation, 180 ml of a normal sodium hydroxide solution (180 mmol) is added dropwise thereto, thus obtaining a pH of 3.5. Thereafter, the batch is heated for two hours to 95° C. and the thus-separated yellow precipitate is suctioned off and washed with water. The moist precipitate is suspended in 200 ml of water and, after adding 1.95 g (10 mmol) of N-methylglucamine, is made to dissolve by heating to 95° C. for four hours. The clear, reddish-brown solution is subsequently concentrated to dryness under vacuum. After drying at 60° C. under vacuum, a brown powder is obtained in a quantitative yield, mp 131–133° C. (foaming).

Analysis ($C_{21}H_{36}FeN_4O_{15}$, M=641): Calculated: C 39.88% H 5.74% N 8.86% Fe 8.83%. Found: C 39.77% H 5.90% N 8.68% Fe 8.80%.

The physioligically compatible paramagnetic compounds, e.g., complex salts are utilized in amounts effective to enhance imaging, usually in concentrations of 0.05–500 mmol/l, preferably 0.5–20 mmol/l of the contrast medium.

In order to stabilize the paramagnetic complex salts with respect to the acidic stomach content, it is necessary to add substances which lower the hydrogen ion concentration of the stomach in such a way that the pH is higher than 3 at the location of the medium in the body. Bases, buffers and/or buffer mixtures or base mixtures etc. can be utilized for this purpose, as long as they ensure achievement of this pH range and are physiologically compatible. Suitable agents include, for example, tris(hydroxymethyl)aminomethane (2-amino-2-hydroxymethyl-1,3-propanediol, trometamol), sodium dihydrogen phosphate/disodium hydrogen phosphate, citric acid/disodium phosphate etc., trometamol being preferred. Suitable such compounds are those ensuring a pH of 3–8, preferably 5–8, in the stomach in view of the overall composition of the medium (including optionally added acid to achieve a desirable contrast medium pH of about 7–7.5 as described below.) Typically, the pH of the contrast medium itself will be in the range of 3–8, preferably 5–8. Other suitable base/buffer agents include all physiologically compatible organic and inorganic bases, e.g., sodium carbonate, calcium carbonate, amino sugars (e.g., glucosamine), amino alcohols (e.g., methylglucamine), amino acids (e.g., arginine, lysine), and the like.

Under most circumstances, the pH adjusting buffer or base will be included in the composition of this invention; however, this is not an absolutely necessary ingredient. Whenever the other components of the contrast medium are stable under the respective conditions (e.g., in rectal applications), the base or buffer can be omitted.

These compounds are utilized in amounts effective to maintain the desired pH range, e.g., usually in amounts of about 10–50 mmol per liter of medium.

In order to improve the filling up of the gastrointestinal tract and also for stool solidification, it may be necessary or desirable to add to the medium of this invention materials which raise its viscosity and are physiologically acceptable. Suitable materials having a viscosity-raising effect are well known and all are employable as long as they are compatible with this invention, e.g., natural, high-molecular weight carbohydrates, such as alginates, xanthan gum, pectin, tragacanth, bassorin, guar, karaya, gum arabic, etc. or polypeptides, such as casein and gelatin, etc. or semisynthetic, high-molecular weight carbohydrates, such as microcrystalline cellulose, sodium carboxymethylcellulose, methylcellulose, and the hydroxyalkyl derivatives thereof, such as methylhydroxyethylcellulose, etc. or expandable silicates, such as bentonite and colloidal silicic acid, etc. or the preparations utilized as antidiarrheics etc. See, e.g., the U.S. Pharmacopie.

The optional viscosity-raising materials are used in amounts which are effective for the purposes discussed, generally in an amount of 2–40 grams per liter, preferably 10–30 grams per liter of medium.

Particularly preferred enteral contrast media comprise: (a) as the physiologically compatible paramagnetic compound, iron(III) compounds or complex salts of aminopolyacids and the ions of the lanthanide elements of atomic numbers 57–70 or the ions of the transition metals of atomic numbers 21–29, 42, and 44, and optionally an inorganic or organic base; (b) as the physiologically compatible, osmotically active substances, mannitol, sorbitol in an amount of 5–70 grams per liter; (c) as the optionally present viscosity-raising material, natural or semisynthetic, high-molecular weight carbohydrates, polypeptides, or expandable silicates in an amount of 2–40 grams per liter; (d) as the viscosity-raising material, natural, high-molecular weight carbohydrates, such as tragacanth, bassorin, guar, or methylhydroxyethylcellulose; (e) as the viscosity-raising material, semisynthetic, high-molecular weight carbohydrates, such as sodium carboxymethylcellulose or methylcellulose, and the hydroxyalkyl derivatives thereof, such as methylhydroxyethylcellulose; (f) as the physiologically compatible complex salt, the di-N-methylglucamine salt, the disodium salt, or the N-methylglucamine-sodium mixed salt of the gadolinium(III) complex of diethylenetriamine pentaacetic acid or the di-N-methylglucamine salt of the iron(III) complex of diethylenetriamine pentaacetic acid; (g) the di-N-methylglucamine salt, the disodium salt, or the N-methylglucamine-sodium mixed salt of the gadolinium(III) complex of diethylenetriamine pentaacetic acid, together with mannitol and tris(hydroxymethyl)aminomethane (trometamol); (h) 0.05–5 millimoles per liter of di-N-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, and 20–60 grams per liter of mannitol in water; (i) 0.05–5 millimoles per liter of di-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, 20–60 grams per liter of mannitol, and 5–30 grams per liter of methylhydroxyethylcellulose ("Methocel") in water; and (j) 0.05–5 millimoles per liter of di-N-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, 20–60 grams per liter of mannitol, and 2–20 grams per liter of tragacanth in water.

The contrast media of this invention can be utilized in mammals and other animals, including humans, for (a) examination of a wide variety of structural and functional features of the gastrointestinal tract itself, e.g., lesions and other features of the large intestine, e.g., of the rectum or colon, also by rectal administration in which case the contrast medium is suitably introduced into an emptied intestine, as well as features of the small intestine and the stomach, etc.; and (b) for identification, e.g., of the esophagus, stomach and intestine within the respective NMR tomograms and for differentiation of tissues in organs located very close to the intestine (e.g., pancreas, lymph nodules etc.

The paramagnetic compound can be dissolved in the aqueous medium of this invention or can be conventionally suspended or otherwise dispersed therein. The same is also true for the other ingredients of the contrast medium. However, it is preferred that the ingredients be dissolved in the medium and this will generally be the case, especially for the osmotically active agent.

This invention also concerns a process for the preparation of the novel enteral contrast media useful for nuclear spin tomography wherein in a manner known per se, a granulated material containing at least one physiologically compatible paramagnetic complex salt is dissolved or suspended in water together with a physiologically compatible, osmotically active substance, as well as a physiologically compatible base/buffer or buffer mixture yielding a pH of 3–8 in the medium and, optionally, additionally a physiologically compatible, viscosity-raising material.

For example, in order to prepare the novel media, 65 g to 70 g of the granulated material containing the contrast medium is mixed with 1 liter of water, and the resultant suspension and/or solution is introduced into the gastrointestinal tract from a time immediately after preparation up to 5 minutes thereafter at the latest; this is done by swallowing or by means of an esophageal tube. Per kilogram of body weight, 2 ml to 30 ml of contrast medium are usually administered.

The granulated material used in preparing the contrast medium is obtained by conventionally mixing the osmotically active substance, optionally with the viscosity-raising material and, if desired, with flavoring agents, and passing it through a sieve (e.g., 18–45 mesh) When the viscosity-raising material is present, the mixing step is repeated. A powder is obtained which is moistened and triturated with such a quantity of a granulating solution that the thus-produced moist granulated material can then once more be passed through a sieve (e.g., 18–45 mesh).

The granulating solution is preferably obtained by dissolving the paramagnetic complex salt with the buffer compound and meglumine in water, adjusting the pH with dilute inorganic acid (preferably HCl) to a value of 7.4–7.5 preferably, i.e., selecting the base/buffer system appropriately, and filling to the desired volume with water.

After the powder has been moistened and triturated with this granulating solution, as described above, it is again passed through a sieve (e.g., 18–45 mesh); the screened material is dried at about 50° C., under reduced pressure (about 200 torr) for 1.5–3 hours. The dried granulated material is smoothed out by another screening step, and is finally mixed (stirred or otherwise agitated) one more time. In this way, 65–70 g of granulated material is obtained, yielding a ready-for-use medicine upon dissolution in 1 liter of water.

The medium of this invention can also contain any conventional pharmacologically acceptable adjuvant which is compatible with NMR imaging, especially those employable in enteral (e.g., oral or rectal) administration.

Without further elaboration, it is believed that one skilled in the art can, using the preceding description, utilize the present invention to its fullest extent. The following preferred specific embodiments are, therefore to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following operating directions further demonstrate the use of the novel contrast media of this invention in greater detail.

With the aid of a catheter, 5 ml of a contrast medium having the following composition is administered to a male Sprague-Dawley rat weighing about 400 g:
1 mmol/l gadolinium complex of diethylenetriamine pentaacetic acid as the di-N-methylglucamine salt
20 mmol/l trometamol
45 g/l mannitol.

The solution was adjusted to pH =7.2 with 1N hydrochloric acid.

After administration, the animal is anesthetized by intraperitoneal injection of sodium pentobarbital (60 mg/kg). Thereafter, horizontal strata are produced at the level of the abdomen of the rat with the aid of a small-animal proton nuclear spin tomograph. In the first pictures, taken about 10 minutes after oral administration, the stomach content is contrasted in white and very readily distinguishable from the parenchymatous organs of the abdomen. In later pictures, intestinal loops can be perfectly imaged. This is possible only due to the addition of the nonabsorbable mannitol. Without this osmotically effective additive, the water is absorbed too quickly, and contrasting of the intestinal lumen is impossible.

PREPARATION EXAMPLE 1

(A) Production of Granulating Solution

A solution is prepared from 743 mg (1 mmol) of mono-N-methylglucamine salt of the gadolinium(III) complex of diethylenetriamine pentaacetic acid (DTPA) with 195.2 mg (1 mmol) of N-methylglucamine and 2.423 g (20 mmol) of tris(hydroxymethyl)aminomethane in 5 ml of water; the pH is adjusted to 7.4–7.5 with 1N hydrochloric acid, and a volume of 10 ml is provided by filling up with water.

(B) 45 g of mannitol and 20 g of methylhydroxyethylcellulose is mixed for about 3 minutes; the mixture is passed through a 25 mesh sieve, and again mixed for 3 minutes. Then the resultant powder is moistened and triturated in portions with the granulating solution (10 ml) prepared according to (A); the moist granulated material is passed through a sieve with mesh width of 1.25 mm, then dried for 2 hours at 50° C. and under 27 kPa (200 torr), smoothed out through an 18 mesh sieve, and finally mixed for another 3 minutes. The resultant granulated material is combined, for usage purposes, with 1 liter of water and utilized within 5 minutes of preparation.

PREPARATION EXAMPLE 2

(A) Production of Granulating Solution

A solution of 743 mg (1 mmol) of mono-N-methylglucamine salt of the gadolinium(III) complex of diethylenetriamine pentaacetic acid (DTPA), 195.2 mg (1 mmol) of N-methylglucamine, and 2.423 g (20 mmol) of tris(hydroxymethyl)aminomethane in 5 ml of water is brought to pH 7.4 to 7.5 with 1N hydrochloric acid and filled up to a volume of 10 ml.

(B) 55 g of mannitol is passed through a 25 mesh sieve and moistened and triturated in portions with the granulating solution (10 ml) prepared according to (A), the further procedure being as described in Preparation Example 1 under (B).

PREPARATION EXAMPLE 3

(A) The granulating solution is produced as set forth in Preparation Example 1 under (A).

(B) 45 g of mannitol, previously passed through a 45 mesh sieve, and 5 g of tragacanth are mixed for about 3 minutes; the mixture is passed through a 25 mesh sieve, and this mixture is moistened with the granulating solution prepared according to (A). The moist granulated material is further processed as described in Preparation Example 1 under (B) and finally passed through a 25 mesh sieve.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An enterally administrable aqueous contrast medium useful for proton NMR imaging of a body cavity, comprising an amount of a physiologically compatible, paramagnetic compound effective to enhance the contrast of a proton NMR image; an amount of a compound different therefrom which is compatible both physiologically and with NMR imaging and which is substantially not absorbed by the tissue surrounding the body cavity, whereby the osmotic pressure in the contrast medium in the body is substantially the same as or is greater than that in the adjacent tissue of the body cavity such that water absorption out of the body cavity is substantially retarded or eliminated; and an amount of a physiologically compatible base or buffer effective to maintain a pH of 3–8 in the contrast medium in the body cavity.

2. An enterally administrable aqueous contrast medium useful for proton NMR imaging of a body cavity, comprising an amount of a physiologically compatible, paramagnetic compound effective to enhance the contrast of a proton NMR image, and an amount of a compound different therefrom which is compatible both physiologically and with NMR imaging and which is substantially not absorbed by the tissue surrounding the body cavity, whereby the osmotic pressure in the contrast medium in the body is substantially the same as or is greater than that in the adjacent tissue of the body cavity such that water absorption out of the body cavity is substantially retarded or eliminated.

3. A contrast medium of claim 1 further comprising a viscosity effective amount of a physiologically compatible viscosity raising agent.

4. A contrast medium of claim 2 further comprising a viscosity effective amount of a physiologically compatible viscosity raising agent.

5. A contrast medium of claim 1, wherein the physiologically compatible paramagnetic compound is an iron(III) compound or is a salt of a complex of an aminopolyacid and an ion of the lanthanide series of an atomic number of 57–70 or of a transition metal of an atomic number of 21–29, 42 or 44.

6. A contrast medium of claim 5, wherein the cation of said salt is derived from an inorganic or organic base.

7. A contrast medium of claim 1, wherein the physiologically compatible, osmotically active substance is mannitol or sorbitol in an amount of 5–70 grams per liter of contrast medium.

8. A contrast medium of claim 3, wherein the viscosity-raising material is a natural or semisynthetic, high-molecular weight carbohydrate, a polypeptide, or an expandable silicate, each in an amount of 2–40 grams per liter of medium.

9. A contrast medium of claim 8, wherein the viscosity-raising material, is a natural, high-molecular weight carbohydrate which is tragacanth, bassorin, guar, or methylhydroxyethylcellulose.

10. A contrast medium of claim 8, wherein the viscosity-raising material is a semisynthetic, high-molecular weight carbohydrate which is sodium carboxymethylcellulose or methylcellulose, or a hydroxyalkyl derivative thereof.

11. A contrast medium of claim 1, wherein the physiologically compatible complex salt is the di-N-methylglucamine salt, the disodium salt, or the N-methylglucaminesodium mixed salt of the gadolinium(III) complex of diethylenetriamine pentaacetic acid, or the di-N-methylglucamine salt of the iron(III) complex of diethylenetriamine pentaacetic acid.

12. A contrast medium of claim 1, wherein the physiologically compatible complex salt is the di-N-methylglucamine salt, the disodium salt, or the N-methylglucaminesodium mixed salt of the gadolinium(III) complex of diethylenetriamine pentaacetic acid.

13. A contrast medium of claim 1, comprising the di-N-methylglucamine salt, the disodium salt, or the N-methylglucamine-sodium mixed salt of the gadolinium(III) complex of diethylenetriamine pentaacetic acid, mannitol and tris(hydroxymethyl)aminomethane.

14. A contrast medium of claim 12, comprising 0.05–5 millimoles per liter of the di-N-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, and 20–60 grams per liter of mannitol in water.

15. A contrast medium of claim 12, comprising 0.5–5 millimoles per liter of the di-N-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, 20–60 grams per liter of mannitol, and 5–30 grams per liter of methylhydroxyethylcellulose in water.

16. A contrast medium of claim 12, comprising 0.05–5 millimoles per liter of the di-N-methylglucamine salt, disodium salt, or N-methylglucamine-sodium mixed salt of the gadolinium(III) complex of diethylenetriamine pentaacetic acid, 10–50 millimoles per liter of tris(hydroxymethyl)aminomethane, 20–60 grams per liter of mannitol, and 2–20 grams per liter of tragacanth in water.

17. A contrast medium of claim 1, wherein the amount of paramagnetic compound is 0.05–500 mmol/l, the amount of osmotically active compound is 5–70 g/l, and the amount of base or buffer is 10–50 mmol/l.

18. A contrast medium of claim 3, wherein the amount of paramagnetic compound is 0.05–500 mmol/l, the amount of osmotically active compound is 5–70 g/l, the amount of base or buffer is 10–50 mmol/l, and the amount of viscosity raising agent is 2–40 g/l.

19. A pharmaceutical kit for preparation of an enterally administrable contrast medium for use in NMR diagnosis, containing
one component comprising a physiologically compatible paramagnetic compound and a physiologically compatible base or buffer system for the pH range 3–8; and
another component comprising a compound compatible both physiologically and with NMR diagnosis and which is substantially not absorbed by the tissue of the gastrointestinal tract.

20. In a method of imaging a body cavity of a patient by performing an NMR diagnosis after administration to the patient of a physiologically acceptable NMR contrast medium, the improvement wherein the contrast agent is that of claim 1.

21. In a method of imaging a body cavity of a patient by performing an NMR diagnosis after administration to the patient of a physiologically acceptable NMR contrast medium, the improvement wherein the contrast agent is that of claim 3.

22. A contrast medium of claim 1 which is adapted for oral administration.

23. A contrast medium of claim 1 which is adapted for rectal administration.

24. A method of enhancing the ability of an NMR imaging contrast agent to enhance an NMR image of a body cavity in medical diagnostics, comprising coadministering the NMR imaging contrast agent and an amount of a compound different therefrom which is compatible both physiologically and with NMR imaging and which is substantially not absorbed by the tissue surrounding the body cavity, whereby the osmotic pressure in the constrast medium in the body is substantially the same as or is greater than that in the adjacent tissue of the body cavity such that water absorption out of the body cavity is substantially retarded or eliminated.

* * * * *